United States Patent
Williams et al.

(10) Patent No.: US 9,255,906 B2
(45) Date of Patent: Feb. 9, 2016

(54) METHODS FOR THE ANALYSIS OF GLYCOPROTEINS OR GLYCOPEPTIDES BY MASS SPECTROMETRY

(71) Applicant: Micromass UK Limited, Manchester (GB)

(72) Inventors: Jonathan P. Williams, South Wales (GB); Jeffery Mark Brown, Cheshire (GB)

(73) Assignee: Micromass UK Limited, Wilmslow (GB)

( * ) Notice: Subject to any disclaimer, the term of this patent is extended or adjusted under 35 U.S.C. 154(b) by 29 days.

(21) Appl. No.: 14/049,652

(22) Filed: Oct. 9, 2013

(65) Prior Publication Data

US 2014/0099725 A1    Apr. 10, 2014

(30) Foreign Application Priority Data

Oct. 9, 2012 (GB) .................................. 1218120.2

(51) Int. Cl.
*G01N 33/68* (2006.01)
*G01N 27/62* (2006.01)
*G01N 30/72* (2006.01)
*H01J 49/00* (2006.01)

(52) U.S. Cl.
CPC ............ *G01N 27/62* (2013.01); *G01N 33/6848* (2013.01); *H01J 49/004* (2013.01); *G01N 30/7233* (2013.01)

(58) Field of Classification Search
CPC ... G01N 27/62; G01N 33/68; G01N 33/6848; G01N 30/02; G01N 30/72; G01N 30/7233; G01N 30/724; G01N 30/08; H01J 49/004

USPC .................... 436/86, 87, 161, 173, 174, 175; 422/68.1, 70, 98; 250/281, 282, 283

See application file for complete search history.

(56) References Cited

U.S. PATENT DOCUMENTS

2010/0261275 A1* 10/2010 Durocher et al. ............. 435/369
2014/0224974 A1* 8/2014 Kenny et al. .................. 250/282

OTHER PUBLICATIONS

Williams et al. Rapid Commun. Mass Spectrom., vol. 27, Oct. 1, 2013, pp. 2383-2390.*
Miladinovic et al. Analytical Chemistry, vol. 84, May 4, 2012, pp. 4647-4651.*
Liu et al. International Journal of Mass Spectrometry, vol. 325-327, Jun. 21, 2012, pp. 161-166.*

(Continued)

*Primary Examiner* — Maureen Wallenhorst
(74) *Attorney, Agent, or Firm* — Micromass UK Limited

(57) ABSTRACT

A method for the analysis of samples including one or more glycopeptides including the steps of separating one or more glycopeptides using a chromatography system to produce a chromatographic eluent, adding a supercharging reagent to the chromatographic eluent, providing the chromatographic eluent and supercharging reagent to a mass spectrometer, ionizing the chromatographic eluent and supercharging reagent in an ion source to produce glycopeptide ions, performing at least one ion ion reaction on at least some of the glycopeptides ions to produce fragment ions, mass analyzing the fragment ions to produce ion ion reaction mass spectral data, and interpreting the ion ion reaction mass spectral data to provide structural information relating to the glycopeptide.

13 Claims, 10 Drawing Sheets

(56) References Cited

OTHER PUBLICATIONS

Sterling, H.J., "Real-Time Hydrogen/Deuterium Exchange Kinetics via Supercharged Electrospray Ionization Tandem Mass Spectrometry," (Analytical Chemistry), vol. 82, 2010, pp. 9050-9057.

United Kingdom Patent Office Combined Search and Examination Report dated Jun. 19, 2014 for corresponding Application No. GB1317926.2.

* cited by examiner

METHODS FOR THE ANALYSIS OF GLYCOPROTEINS OR GLYCOPEPTIDES BY MASS SPECTROMETRY

CROSS REFERENCE TO RELATED APPLICATIONS

This application claims priority to and benefit of United Kingdom Patent Application No. 1218120.2 filed on Oct. 9, 2012. This application is also related to commonly-assigned United Kingdom Patent Application entitled "A Method for the Analysis of Glycoproteins or Glycopeptides by Mass Spectrometry, filed concurrently on Oct. 9, 2013 (Atty. Docket No. M-1837 GB2). The contents and teachings of each of these applications are hereby expressly incorporated herein by reference in their entirety.

FIELD OF THE INVENTION

This invention relates to the analysis of glycoproteins and glycopeptides by mass spectrometry, and more specifically, to the analysis of glycoproteins and glycopeptides structures, by the combination of Liquid Chromatography and Mass Spectrometry.

BACKGROUND

Glycoproteins are key components in many different functions within the human and animal body. It is often desirable to analyse the structure and sequence of glycoproteins and glycopeptides, in order to get information about health problems including breast cancer in Humans.

The analysis of glycoproteins and glycopeptides can be difficult ordinarily by mass spectrometry. In order to get significant information about any particular glycoprotein or glycopeptide sequence, data based upon the fragmentation of the analyte is required. One method of getting fragmentation data is typically Collision Induced Dissociation (CID), However, CID merely tends to result in the removal of the Glycan related group, which does not provide as much useful data for the sequencing of the Glycoprotein. An alternative method of fragmentation is Electron Transfer Dissociation. (ETD). However, ETD, does not provide much efficient fragmentation under normal conditions, which may also prevent sequencing the glycoprotein.

There is therefore a need for an improved method of analyzing glycoproteins and glycopeptides by Mass spectrometry where more fragments are produced, which allows the generation of data which provides greater sequence detail from which more structural information relating to the glycoprotein or glycopeptides can be deduced.

SUMMARY

In one aspect, a method is provided for the analysis of samples including one or more glycopeptides. In an exemplary embodiment, the method includes separating one or more glycopeptides using a chromatography system to produce a chromatographic eluent, adding a supercharging reagent to the chromatographic eluent, providing the chromatographic eluent and supercharging reagent to a mass spectrometer, ionizing said chromatographic eluent and supercharging reagent in an ion source to produce glycoprotein ions, and operating the mass spectrometer in at least a first mode. The first mode can include performing at least one ion ion reaction on at least some of the glycopeptide ions to produce fragment ions, mass analyzing the fragment ions to produce mass spectral data, and interpreting the mass spectral data to provide structural information relating to the glycopeptide.

In one embodiments, the ion ion reaction can be an Electron Transfer Dissociation reaction. In a second embodiment the ion ion reaction can be an Electron Capture Dissociation reaction. In a further embodiment the ion ion reaction can be a Proton Transfer Reaction.

In exemplary embodiments Electron Transfer Dissociation may be performed using an Electron Transfer Dissociation reagent from the group consisting of Fluoranthene, Azobenzene, 1,4-dicyanobenzene, 1,3-dicyanobenzene and 1,4-nitrotoluene, nitrosobenzene.

The Supercharging reagent can, in exemplary embodiments, be selected from the group comprising m-nitrobenzyl alcohol (m-NBA), sulfolane, dimethyl sulfoxide (DMSO), dimethylformamide (DMF), thiodiglycol, dimethylacetamide, dimethylsulfoxide, and N-methylpyrrolidone, glycerol, acetonitrile.

In some embodiments, the method may further include operating the mass spectrometer in at least a second mode. The second mode can include performing Collision induced dissociation on at least some of the glycoprotein ions to produce Collision induced dissociation fragment ions, mass analyzing the Collision induced dissociation fragment ions to produce Collision induced dissociation mass spectral data, and interpreting the Collision induced dissociation mass spectral data to provide structural information relating to the glycoprotein.

In such embodiments, the method may further comprise operating the mass spectrometer in at least a third mode. The third mode can include performing substantially no fragmentation or reaction on at least some ions and analyzing the glycoprotein ions to produce precursor mass spectral data.

In some embodiments, the method may comprise operating the mass spectrometer in both the first and second modes simultaneously. In another embodiment, the method can include operating the mass spectrometer in the first and second modes consecutively. In some embodiments, the method can include operating the mass spectrometer in the first, second, and third modes consecutively. In other embodiments, the method can include operating the mass spectrometer both the first and second modes simultaneously and in third mode consecutively.

It would be a considerable benefit for the user to be able to get information available from a mass spectrometer in a precursor ion mode, to be able to provide details of precursor ion masses, as well as structural information from data produced in CID mode, and structural information from data produced in ETD mode. In ETD mode, the data produced may give information about the structure of the sequence of the protein or peptide, and in CID mode, the data produced may give further information about the structure of the sugar group.

An advantage to adding the supercharging reagent post separation is that this eliminates the danger of contamination of the chromatography apparatus by the supercharging reagent, which may result in deterioration of performance of the chromatography device. In a preferred embodiment, the addition of the supercharging reagent to the chromatographic eluent may be performed using a mixing tee between the chromatography system and the mass spectrometer.

In another exemplary embodiment, a method is provided for the analysis of samples including one or more glycopeptides. The method includes separating one or more glycopeptides using a chromatography system to produce a chromatographic eluent, adding a supercharging reagent to the chromatographic eluent, providing the chromatographic eluent and supercharging reagent to a mass spectrometer, ionizing said chromatographic eluent and supercharging reagent in an ion source, selecting glycopeptides ions of a higher charge state caused by the supercharging reagent, performing at least one ion ion reaction on at least some of the selected glycopeptides ions to produce fragment ions, and mass analyzing the fragment ions to produce mass spectral data and interpreting the mass spectral data to provide structural information relating to the glycoprotein.

In a further exemplary embodiment a method is provide for the analysis of samples including one or more glycopeptides that can include separating one or more glycopeptides using a chromatography system to produce a chromatographic eluent, adding a supercharging reagent to the chromatographic eluent, providing the chromatographic eluent and supercharging reagent to a mass spectrometer, ionizing said chromatographic eluent and supercharging reagent in an ion source, and operating the mass spectrometer in at least a first mode. The first mode can include selecting glycopeptide ions of a higher charge state caused by the supercharging reagent, performing at least one ion ion reaction on at least some of the selected glycopeptide ions to produce fragment ions, mass analyzing the fragment ions to produce mass spectral data, and interpreting the mass spectral data to provide structural information relating to the glycopeptide.

In another aspect, an apparatus including a chromatography system and a mass spectrometry system is provided to perform the methods disclosed herein. According to exemplary embodiments of the apparatus and methods disclosed herein, the mass spectrometer can include an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further include either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

BRIEF DESCRIPTION OF THE DRAWINGS

Various embodiments of the present invention will now be described, by way of example only, and with reference to the accompanying drawings in which.

DETAILED DESCRIPTION

Immunoglobulins are serum glycoproteins involved in the defense mechanism of the immune system. Trastuzumab is an immunoglobulin G (IgG) recombinant monoclonal antibody drug targeted against the extracellular domain of the human epidermal growth factor receptor 2 (HER2), and is indicated for the treatment of HER2-positive early or metastatic breast cancer.

The manufacture of biopharmaceutical recombinant IgG, a heterogeneous glycoprotein, is a significant challenge. It is known that glycosylation is one of the most important post-translational modifications (PTM) and plays a number of different roles within the cell which affect tertiary structure and potentially therapeutic efficacy. A critical PTM of human IgG is the N-linked glycosylation of the Fc domain. The glycosylation of the Fc domain of recombinant IgG produced in CHO and NS0 cells is mainly characterized by core-fucosylated complex bi-antennary type structures with low levels of galactosylation and sialylation. It is well known that variations in Fc glycosylation affect Fc-mediated effector functions. Therefore, the glycosylation of therapeutic proteins such as monoclonal antibodies (mAb) needs to be closely monitored. A highly consistent PTM profile is particularly important in cases where modifications potentially impact the potency, pharmacokinetics, pharmacodynamics, and immunogenicity of the product.

An ACQUITY UPLC H-Class Bio system (Waters Corporation, Milford, US) was directly coupled to a standard ESI interface of a Synapt G2-S mass spectrometer. Reversed-phase chromatographic separation of 1-10 pmol of tryptic peptides were performed on a BEH300 C18, 1.7 μm, 2.1×150 mm column. Mobile phase A and B were water containing 0.1% formic acid and acetonitrile containing 0.1% formic acid respectively. The tryptic peptides were eluted off column using a gradient from 5-35% B over 35 mins at a flow rate of 100 μL/min. The gradient was further ramped to 50% B for 10 mins then to 80% B for 1 minute and held for 5 minutes at a flow rate of 200 μL/min.

Figure 1:
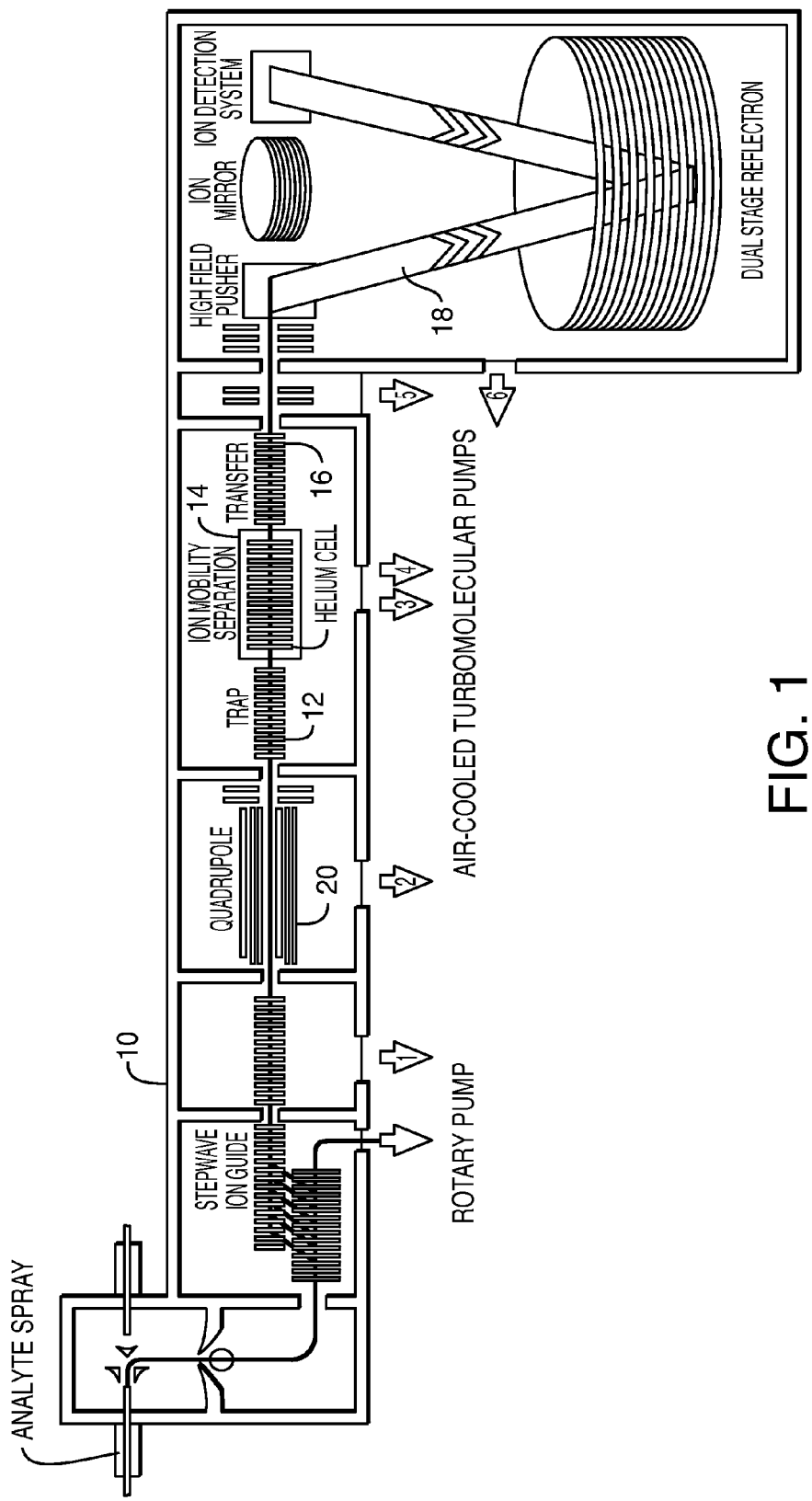
FIG. 1 illustrates of a mass spectrometer suitable to perform the methods of the invention.

ESI-MS was performed on a hybrid quadrupole/ion mobility/oa-ToF mass spectrometer (Synapt G2-S), (Waters Corporation, Manchester, UK) as shown in FIG. 1, the instrument (10) is fitted with electron transfer dissociation (ETD) functionality.

UPLC-MS/MS data independent ($MS^E$) mode of acquisition may be used to test the viability of the tryptic digest of Trastuzumab for glycopeptide detection. In this mode, data was acquired by alternating the ion energy as they enter the collision cell. The ion energy is alternated between a low energy (fixed at 10 eV) and elevated energy (ramped between 15-40 eV). Tandem MS spectra employing CID is usually dominated by glycan-related product ions which hampers peptide sequence information for precise site-specific identification of this important PTM, see FIG. 3.

The high energy spectrum detected abundant oxonium ions at m/z 204 and m/z 366, together with abundant product ions at m/z 126, 138, 168 and 186, thus confirming the presence of glycopeptides [The N-acetylglucosamine (GlcNAc) gives rise to the abundant oxonium ion at m/z 204. Further fragmentation of this ion generates the following ions at m/z 186 (loss of $H_2O$), 168 (loss of $2 \times H_2O$), 138 and 126. The ion at m/z 186 loses 1 water molecule, aromatizing to 5-acetyl-amino-2-hydroxymethylpyrylium ion at m/z 168 which in turn loses formaldehyde ($CH_2O$) to form the 3-acetylamino pyrylium ion at m/z 138. The ion at m/z 168 can also lose ketene ($C_2H_2O$) to form the ion at m/z 126]. The ion at m/z 366 is due to the GlcNAc-Galactose moiety. As a consequence, $MS^E$ provides little peptide sequence information for precise site-specific PTM identification.

Figure 3A:
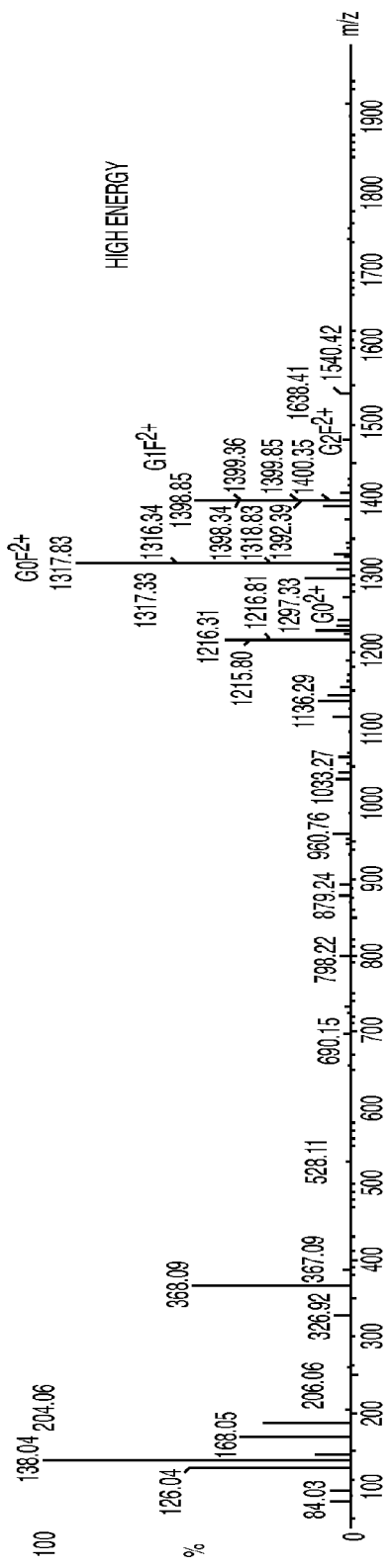
FIG. 3A illustrates a high energy mass spectra showing $MS^E$-CID data of glycopeptide ions produced from Trastuzumab EEQY(N)*STYR.
Figure 3B:
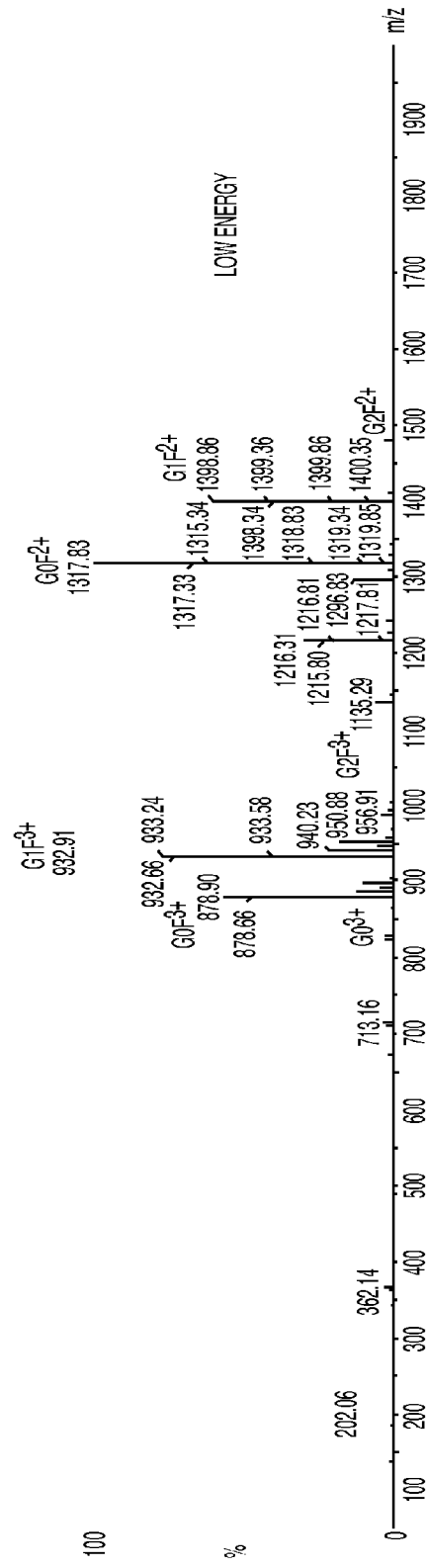
FIG. 3B illustrates a low energy mass spectra showing $MS^E$-CID data of glycopeptide ions produced from Trastuzumab EEQY(N)*STYR.

ETD is a powerful fragmentation technique known to be particularly useful for determining modification sites of labile PTMs, which are often difficult to characterize using CID, as shown in FIG. 3

This therefore, illustrates the need for the present invention, exemplary embodiments of which are described in detail below.

In one embodiment, the instrument comprises three consecutive, gas filled, travelling wave (T-Wave) RF stacked ring ion guides (12, 14, 16) prior to a ToF mass analyser (18). For ETD type fragmentation, a sub-ambient pressure (~2 mbar) glow discharge anion source (not shown) was used to fill the Trap (first) T-Wave cell (12) with quadrupole (20) mass selected ETD reagent anions formed from 1,3-dicyanobenzene (m/z 128). During an acquisition, the source polarity and quadrupole (20) set mass are switched to allow quadruply charged cations formed from addition of m-NBA, using ESI of the peptides to interact with stored reagent anions in the Trap T-Wave (12). This interaction allows an ion-ion type reaction resulting in ETD product ions which if desired can be separated according to their ion mobilities in the second cell (IMS T-Wave cell (14)). Upon exiting the IMS cell the ions enter the (third) Transfer T-Wave cell (16) which can be used to transfer ions into the ToF or optionally provide supplemental activation (CID) prior to the ToF. For efficient ETD, within the Trap T-Wave cell (12), the bath gas used was helium set to a pressure of 0.05 mbar. The Transfer T-Wave cell (16) was pressurised to 0.005 mbar with argon. The T-Wave speed and amplitude which influence the ion-ion interaction time as well as the reaction rate were set to 300 m/sec and 0.2V respectively.

Figure 2:
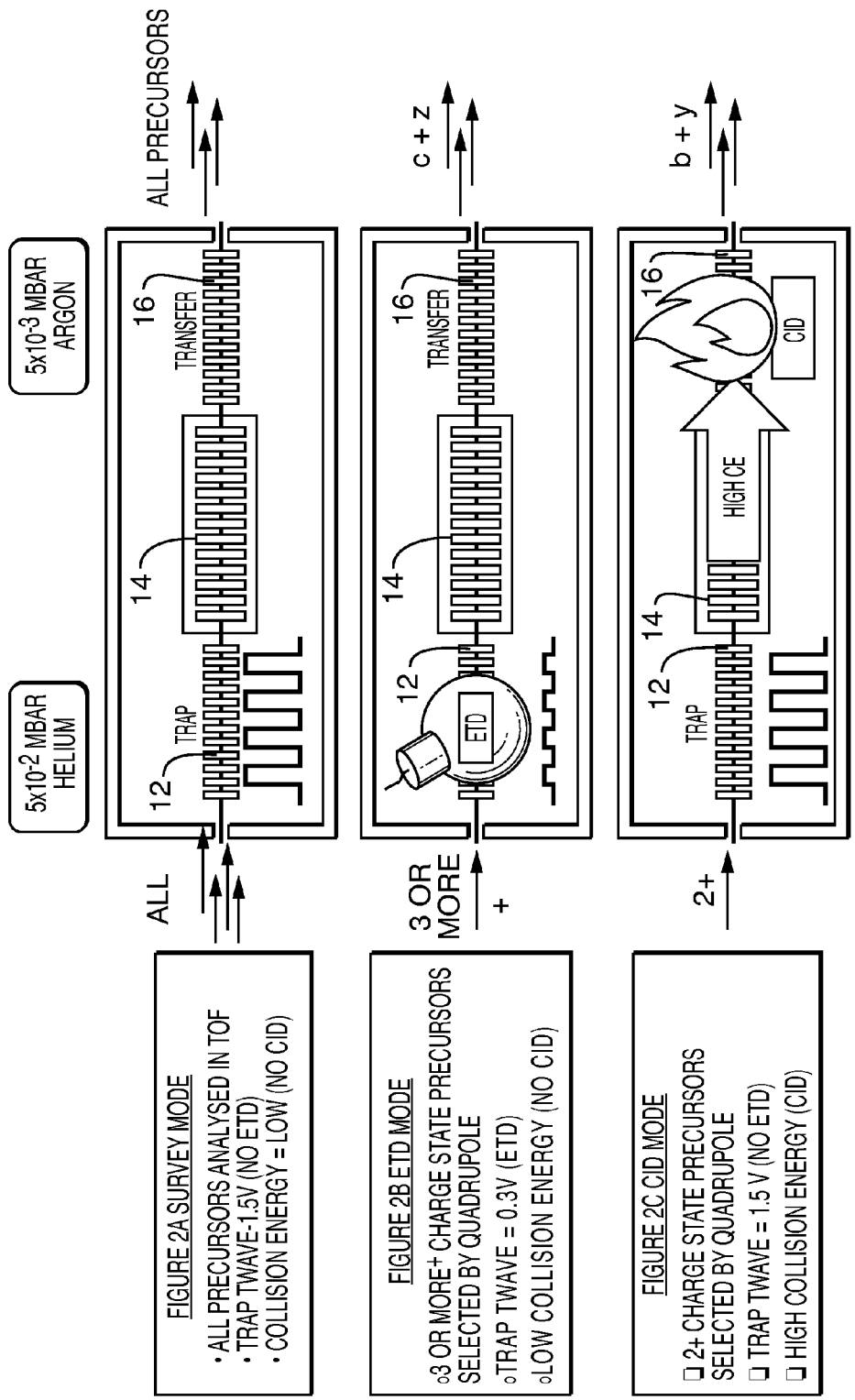
FIG. 2 illustrates several modes of operation that may be performed in accordance with some aspects of the invention.

In a further embodiment, the same instrument, comprising three consecutive, gas filled, travelling wave (T-Wave) RF stacked ring ion guides (12, 14, 16) prior to a ToF mass analyser (18) may be used differently. FIG. 2 demonstrates the different types of fragmentation that is possible in the instrument.

FIG. 2A shows a third mode of operation of a mass spectrometer where precursor ions may be passed to the mass analyser. In this instance, all ions are passed though the quadrupole (not shown). These ions are passed into the first stacked ring ion guide (12), the voltage of the first stacked ring ion guide (12) is set to a high level, which produces no ETD. The ions, are then directed through the second stacked ring ion guide (14) and to the 'transfer' stacked ring ion guide (16). The ions are directed into this device with low energy, which produces no CID, so the precursor ions are then passed to the mass analyser. FIG. 2B shows a first mode of operation of a mass spectrometer where ETD ions may be produced and sent to a mass analyser. In this instance, 3 (or more) + ions are selected by a quadrupole (not shown). The 3 (or more) + ions are passed into the first stacked ring ion guide (12), the voltage of a travelling wave in the first stacked ring ion guide (12) is set to a low level, which produces ETD of the precursor ions. The ions, are then directed through the second stacked ring ion guide (14) and to the 'transfer' stacked ring ion guide (16). The ions are directed into this device with low energy, which produces no CID, so all the ions passed to the mass analyser have been subjected to ETD.

FIG. 2C shows a second mode of operation of a mass spectrometer where CID ions may be produced and sent to a mass analyser. In this instance, 2+ ions are selected by a quadrupole (not shown). The 2+ ions are passed into the first stacked ring ion guide (12) the voltage of a travelling wave in the first stacked ring ion guide (12) is set to a high level, which produces no ETD. The ions, are then directed through the second stacked ring ion guide (14) and to the 'transfer' stacked ring ion guide (16). The ions are directed into this device with high energy, which produces CID of the precursor ions, so all the ions passed to the mass analyser have been subjected to CID.

The three modes of operation could be performed in sequence in the order above, or any other order on a scan by scan basis. The consecutive stepping between these modes may allow extra information to be produced from the sample.

In other embodiments, it may be possible to perform both CID and ETD in the same scan—ie the first and second modes of the mass spectrometer simultaneously. In this embodiment the quadrupole may allow all 2 or more + ions to pass through. These ions are passed into the first stacked ring ion guide (12) the voltage of a travelling wave in the first stacked ring ion guide (12) is set to a low level, which produces ETD upon the 3 or more + ions. The ions, are then directed through the second stacked ring ion guide (14) and to the 'transfer' stacked ring ion guide (16). The ions are directed into this device with high energy, which produces CID of the 2+ precursor ions. This may allow the ions passed to the mass analyser have been subjected to either ETD or CID, dependent upon the charge state of the ions.

In this embodiment, the performance of a precursor scan may be performed as per the description of FIG. 2A. This would assist in the interpretation of the spectra formed from the CID and ETD fragments.

The mass spectrometer can be operated in the three modes described above consecutively. The operator may choose to perform the analysis in the three modes in any order without this having a negative effect ton the mass spectrometer.

In order to show some of the different aspects of the invention, some experimental data is provided, to illustrate potential uses of the invention. It should be appreciated that the actual instruments used are merely examples of instruments that may be used to perform the invention. In principal any chromatography system and many mass spectrometers may be used, or adapted to be used to perform at least some aspects of the invention.

ETD is a radical-driven fragmentation technique and results in cleavage of the peptide N-Cα bond to give c and z•peptide fragment ions (cf. b and y" ions using CID).

Figure 4:
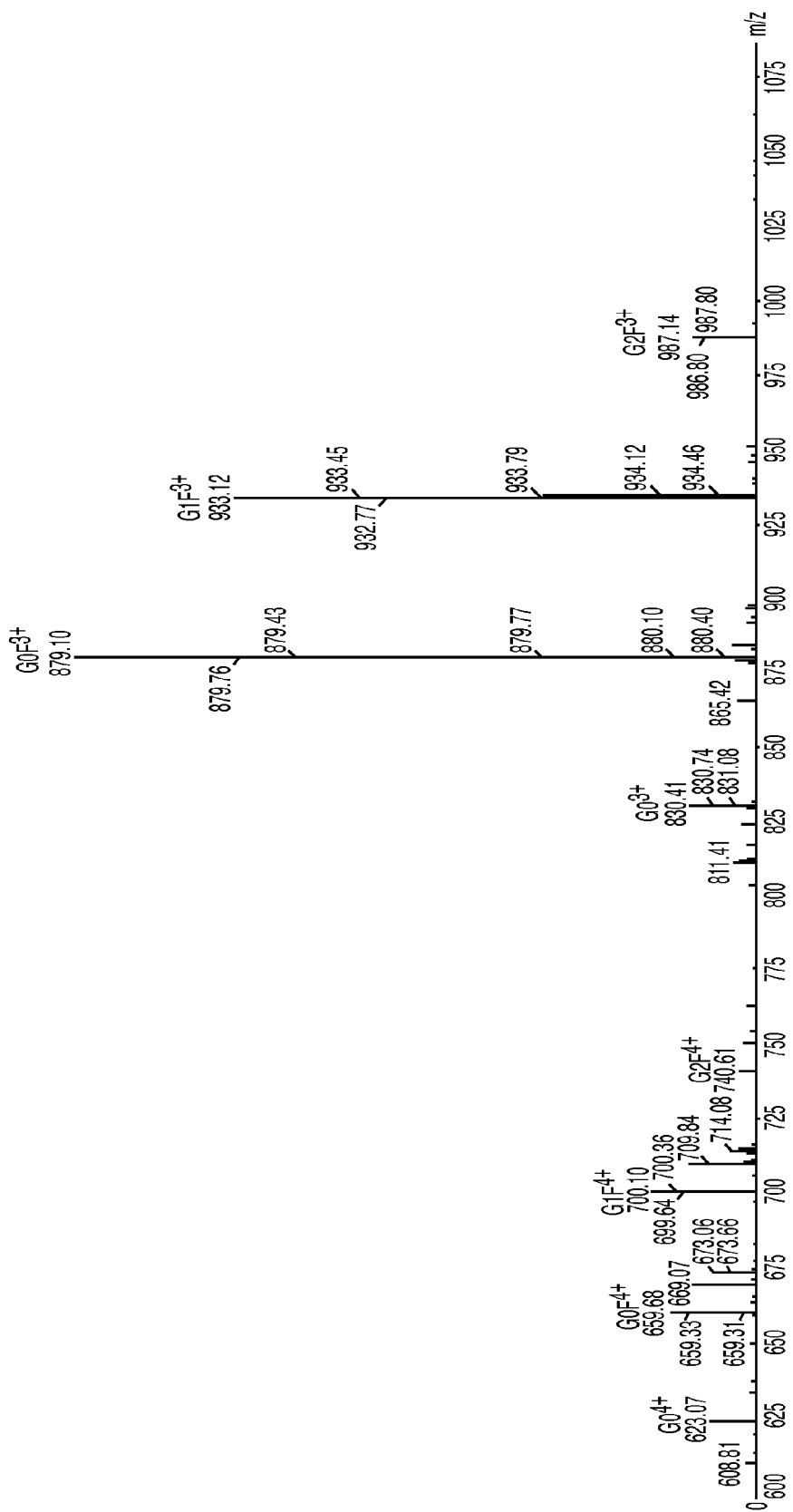
FIG. 4 illustrates a mass spectra showing the detection of quadruply charged tryptic glycopeptide ion of m/z 623 (G0), 659 (G0F), 700 (G1F) and 740 (G2F) using m-NBA for ETD.

During the ETD analysis, ETD was performed on the quadruply charged tryptic glycopeptide ion of m/z 623 (G0), 659 (G0F), 700 (G1F) and 740 (G2F). The quadruply charged ions, the presence of which are illustrated in FIG. 4, were formed through post-column addition of 0.4% m-nitrobenzyl alcohol via a Valco 'T-piece'. The presence of these quadruply charged tryptic glycopeptides ions would not be present in substantial amounts without the addition of m-NBA.

Figure 5:
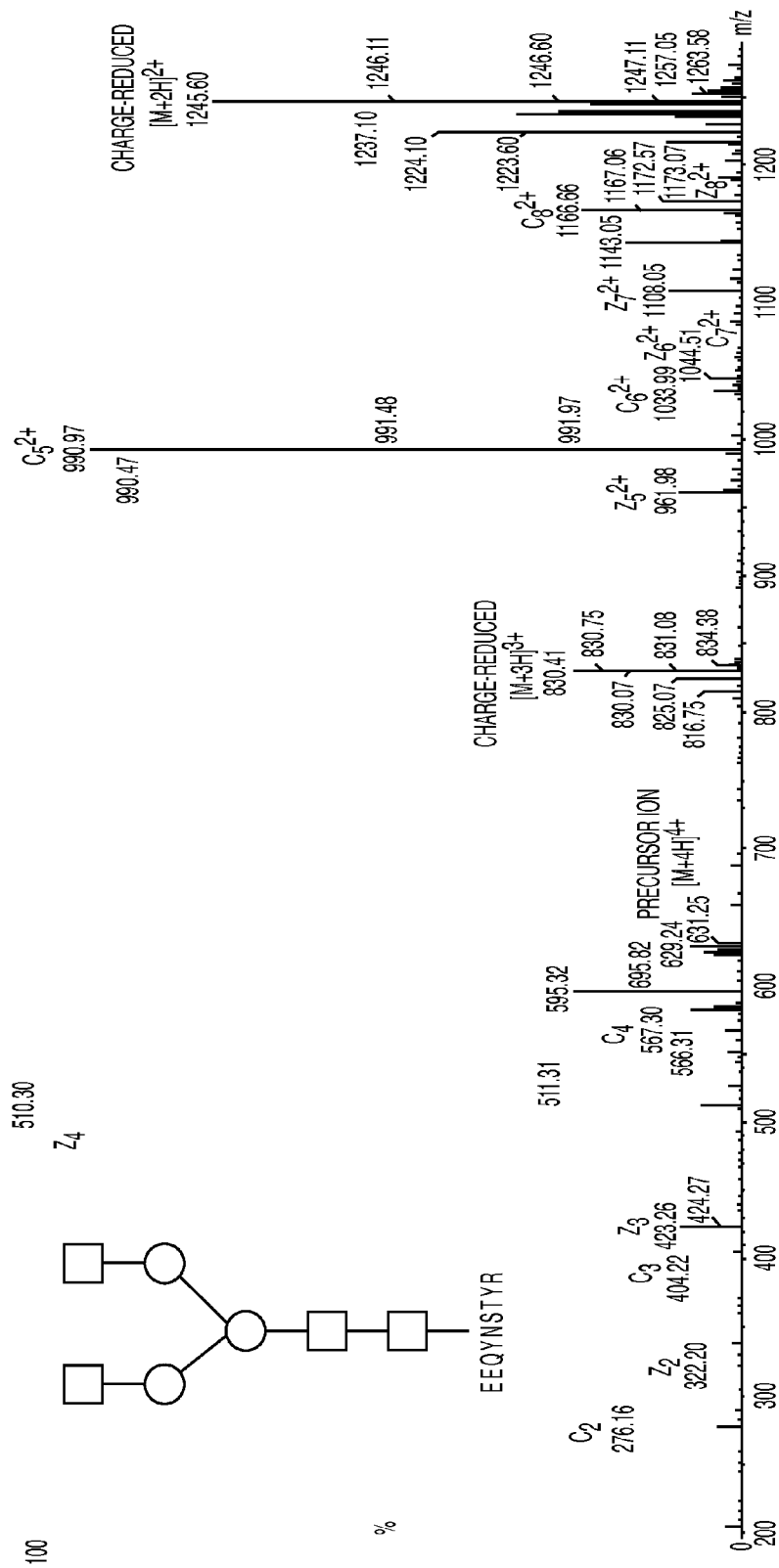
FIG. 5 illustrates a mass spectra showing ETD data of the quadruply charged tryptic glycopeptide ion of m/z 623.

The glycosylated peptide contains nine residues. Following ETD of the quadruply-charged ion of m/z 623 (G0) full sequence information was obtained, as shown in FIG. 5. N-terminal, c ions (even-electron) were detected for $c_2^+$-$c_4^+$ and $c_5^{2+}$-$c_8^{2+}$. Odd-electron, C-terminal ions were detected for $z_1^+$-$z_4^+$, and $z_5^{2+}$-$z_8^{2+}$. The mass difference between $c_4^+$ and $c_5^{2+}$ together with $z_4^+$ and $z_5^{2+}$ clearly shows the mass of the glycosylated asparagine residue (G0). Thus, in contrast to the CID mass spectrum, the ETD-generated mass spectrum provides precise identification of the N-linked binding site.

Figure 6:
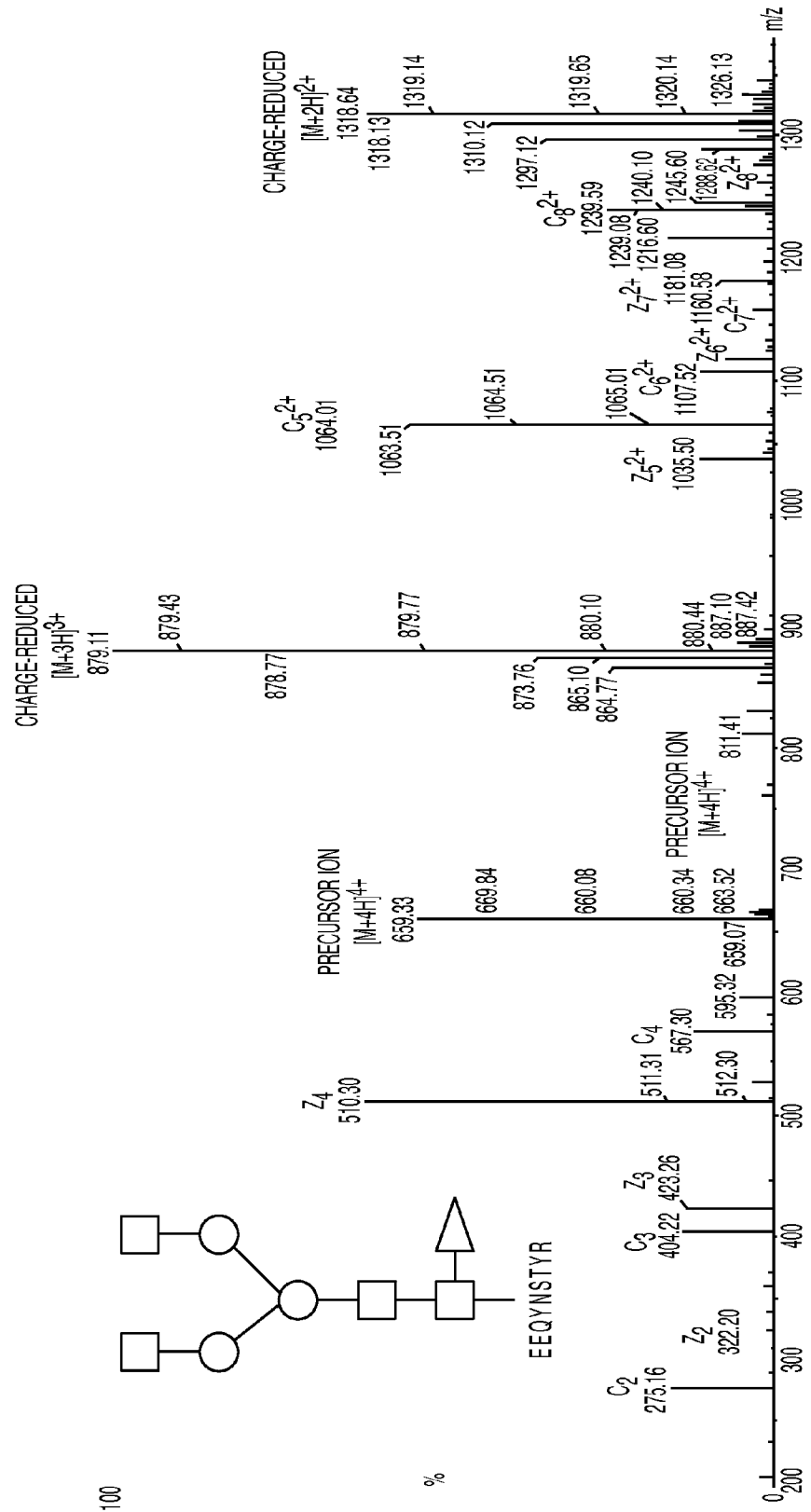
FIG. 6 illustrates a mass spectra showing ETD data of the quadruply charged tryptic glycopeptide ion of m/z 659.
Figure 7:
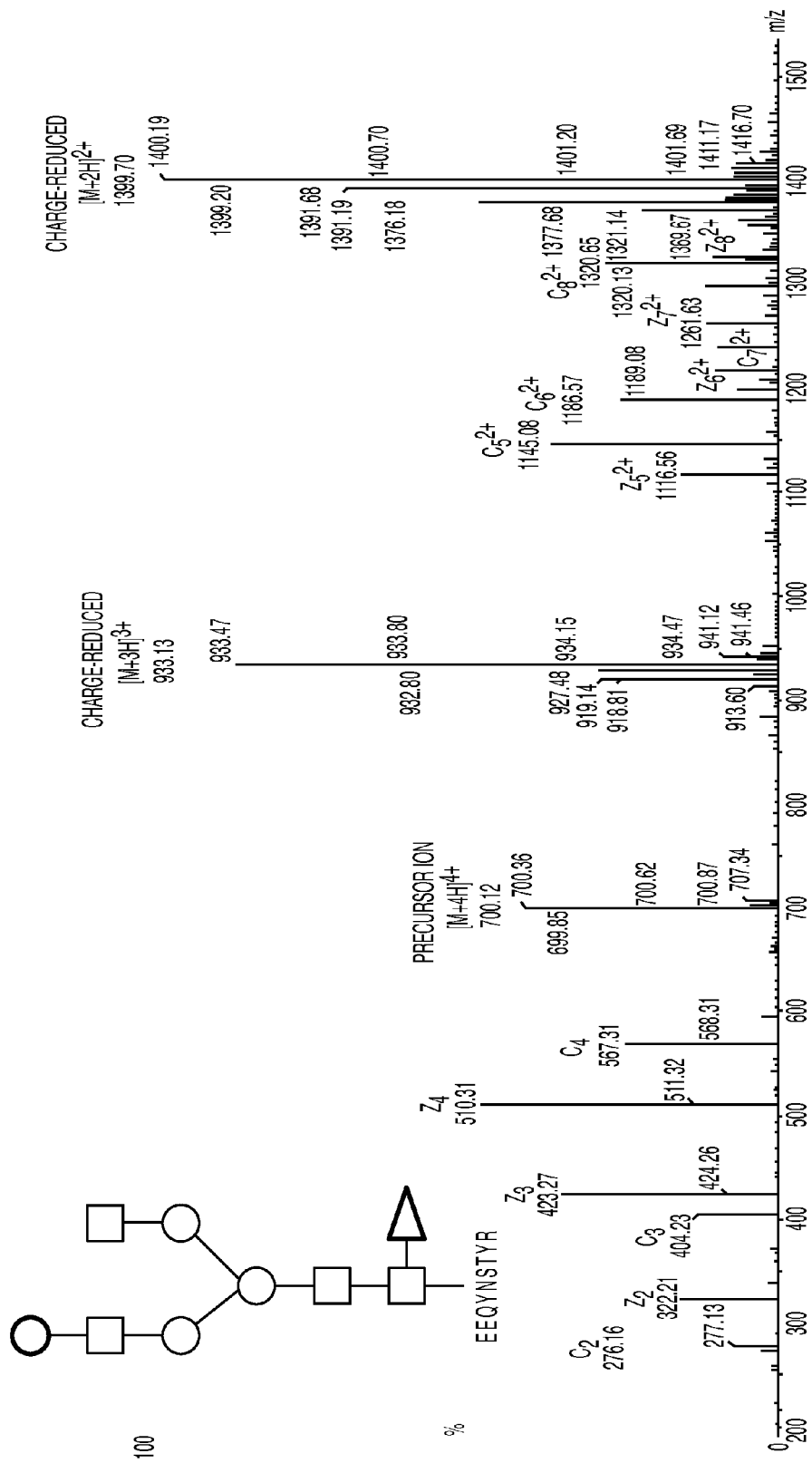
FIG. 7 illustrates a mass spectra showing ETD data of the quadruply charged tryptic glycopeptide ion of m/z 700.

Following ETD of the quadruply-charged ion of m/z 659 (G0F) full sequence information was obtained, as shown in FIG. 6. N-terminal, c ions (even-electron) were detected for $c_2^+$-$c_4^+$ and $c_5^{2+}$-$c_8^{2+}$. Odd-electron, C-terminal ions were detected for $z_1^+$-$z_4^+$, and $z_5^{2+}$-$z_8^{2+}$. The mass difference between $c_4^+$ and $c_5^{2+}$ together with $z_4^+$ and $z_5^{2+}$ clearly shows the mass of the glycosylated asparagine residue (G0F). Thus, in contrast to the CID mass spectrum, the ETD-generated mass spectrum provides precise identification of the N-linked binding site Following ETD of the quadruply-charged ion of m/z 700 (G1F) full sequence information was obtained, as shown in FIG. 7. N-terminal, c ions (even-electron) were detected for $c_2^+$-$c_4^+$ and $c_5^{2+}$-$c_8^{2+}$. Odd-electron, C-terminal ions were detected for $z_1^+$-$z_4^+$, and $z_5^{2+}$-$z_8^{2+}$. The mass difference between $c_4^+$ and $c_5^{2+}$ together with $z_4^+$ and $z_5^{2+}$ clearly shows the mass of the glycosylated asparagine residue (G1F). Thus, in contrast to the CID mass spectrum, the ETD-generated mass spectrum provides precise identification of the N-linked binding site.

Figure 8:
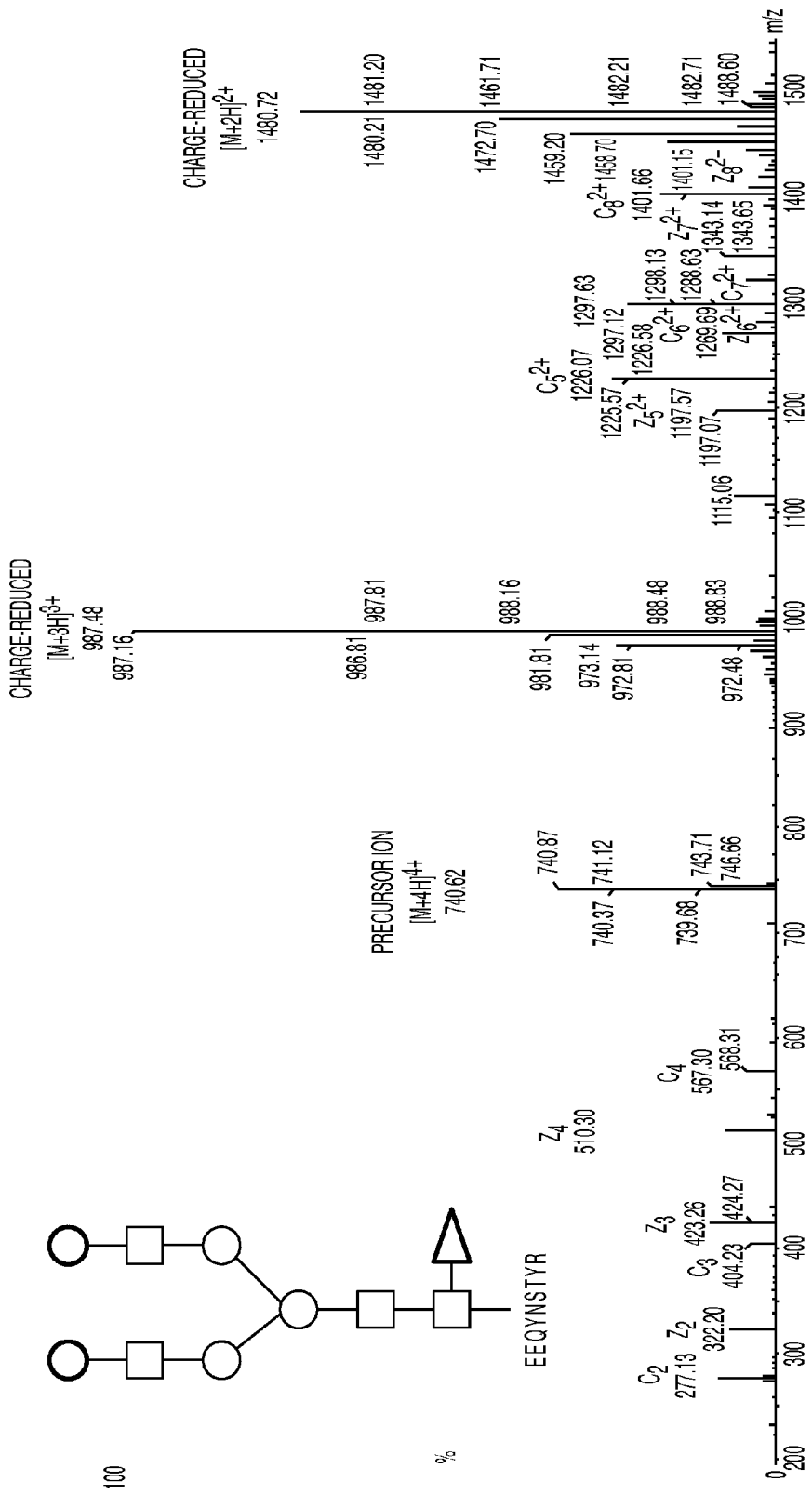
FIG. 8 illustrates a mass spectra showing ETD data of the quadruply charged tryptic glycopeptide ion of m/z 740.

Following ETD of the quadruply-charged ion of m/z 740 (G2F) full sequence information was obtained, as shown in FIG. 8. N-terminal, c ions (even-electron) were detected for $c_2^+$-$c_4^+$ and $c_5^{2+}$-$c_8^{2+}$. Odd-electron, C-terminal ions were detected for $z_1^+$-$z_4^+$, and $z_5^{2+}$-$z_8^{2+}$. The mass difference between $c_4^+$ and $c_5^{2+}$ together with $z_4^+$ and $z_5^{2+}$ clearly shows the mass of the glycosylated asparagine residue (G2F). Thus, in contrast to the CID mass spectrum, the ETD-generated mass spectrum provides precise identification of the N-linked binding site.

Figure 9:
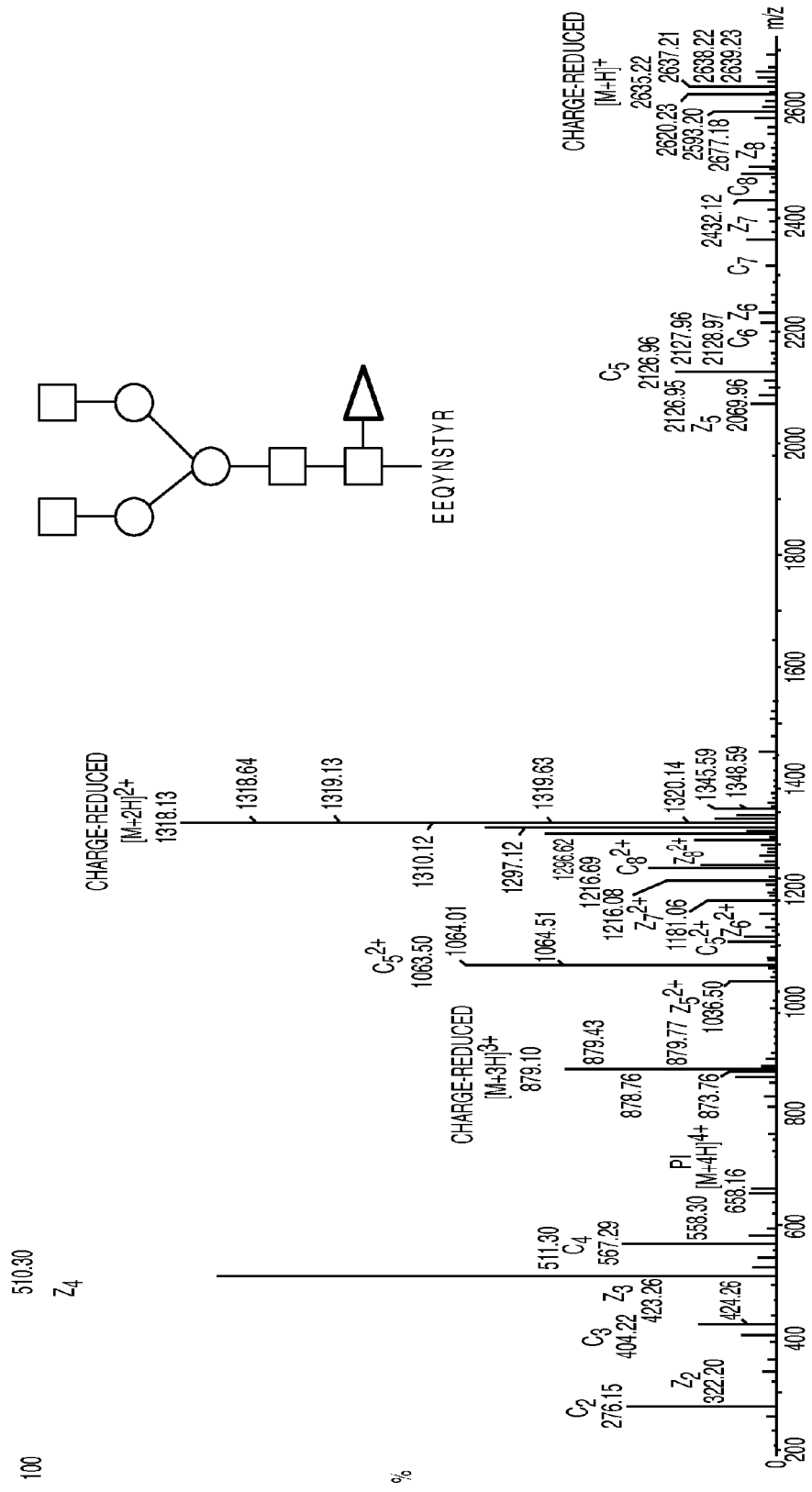
FIG. 9 illustrates a mass spectra showing ETD data of the quadruply charged tryptic glycopeptide ion of m/z 659.

Following ETD of the quadruply-charged ion of m/z 659 (G0F) full sequence information was obtained over the wider m/z range from 200-2800, as shown in FIG. 9. N-terminal, c ions (even-electron) were detected for $c_2^+$-$c_8^+$ and $c_5^{2+}$-$c_8^{2+}$. Odd-electron, C-terminal ions were detected for $z_1^+$-$z_8^+$, and $z_5^{2+}$-$z_8^{2+}$. The mass difference between $c_4^+$ and $c_5^+$ together with $z_4^+$ and $z_5^+$ clearly shows the mass of the glycosylated asparagine residue (G0F). Thus, in contrast to the CID mass spectrum, the ETD-generated mass spectrum provides precise identification of the N-linked binding site.

Figure 10:
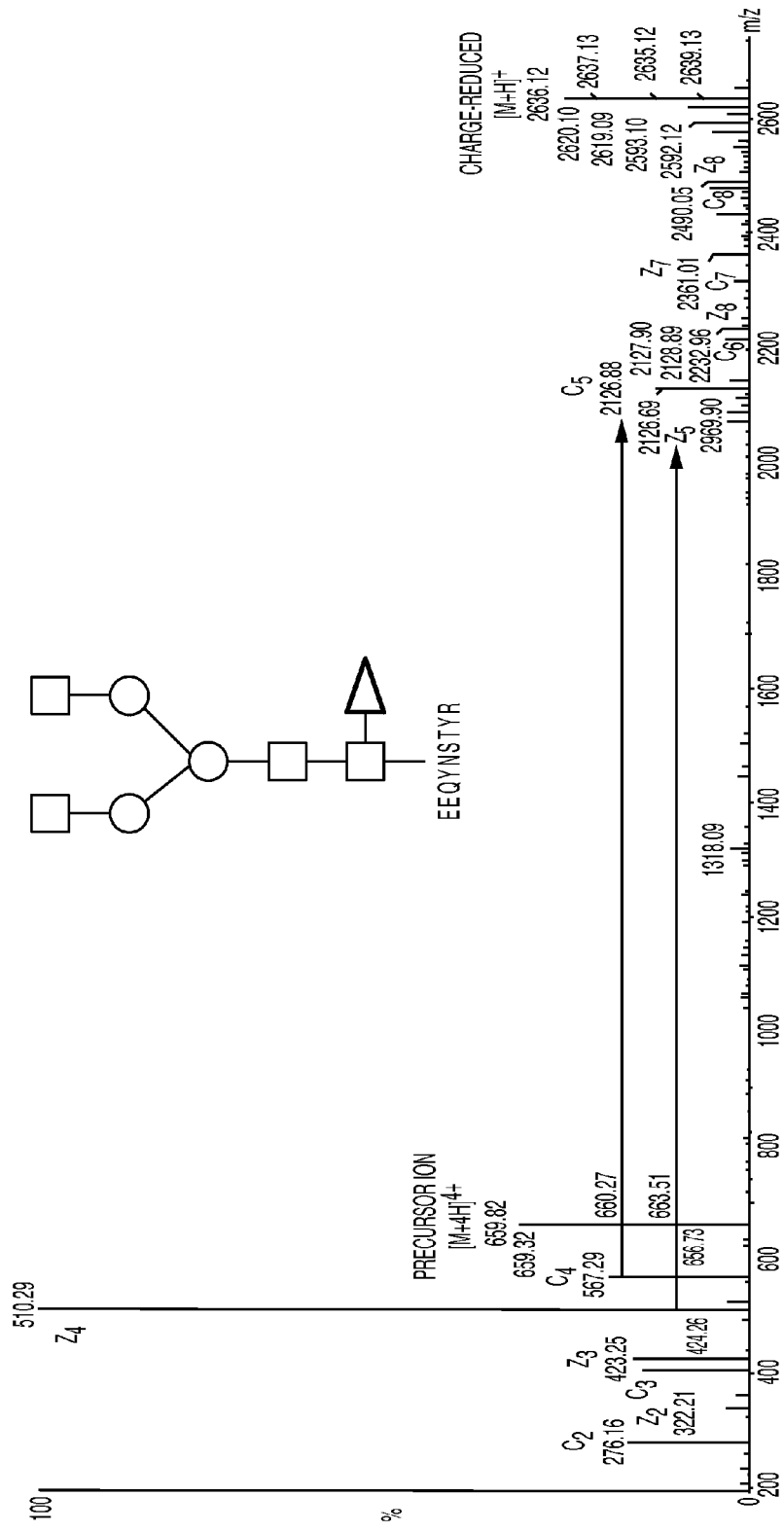
FIG. 10 illustrates a mass spectra showing ETD data of the quadruply charged tryptic glycopeptide ion of m/z 659.

Following a minimal re-tune of the ETD parameters, the quadruply-charged ion of m/z 659 (G0F) was again selected to undergo ETD. As can be seen, full sequence information was obtained m/z range 200-2800, see FIG. 10. N-terminal, c ions (even-electron) were detected for $c_2^+$-$c_8^+$. Odd-electron, C-terminal ions were detected for $z_1^+$-$z_8^+$. The mass difference between $c_4^+$ and $c_5^+$ together with $z_4^+$ and $z_5^+$ clearly shows the mass of the glycosylated asparagine residue (G0F). Again, in contrast to the CID mass spectrum, the ETD-generated mass spectrum provides precise identification of the N-linked binding site.

The present invention is illustrated using the combination of Liquid chromatography with mass spectrometry and the implementation of ETD as an alternative fragmentation technique to low-energy CID is better suited for the site-specific determination of PTM's, in this case N-linked glycosylation of Trastuzumab. Following ETD of the four N-linked glycoforms shown, full sequence information was obtained in all cases without the requirement of magnification of the m/z scale. The Synapt G2-S with ETD implementation is highly sensitive and combined with a low-pressure glow discharge source for anion generation is a particularly attractive option for the determination of labile PTM's of therapeutic monoclonal antibodies.

Any ETD reagent may be used. Preferred reagents may include Fluoranthene, Azobenzene, 1,4-dicyanobenzene, 1,3-dicyanobenzene, 1,4-nitrotoluene and nitrosobenzene.

The mass spectrometer may be a linear (2D) ion trap mass spectrometer, a linear (2D) ion trap in combination with an orbitrap, a hybrid quadrupole/ion mobility/oa-ToF mass spectrometer, a 3D ion trap, or any other type of instrument suitable of performing ion-ion reactions.

The term Glycopeptide as used throughout the specification and claims may refer to Glycoproteins, Glycopeptides, or any mix of both Glycoproteins and Glycopeptides.

The term ions of a higher charge state caused by the supercharging reagent refers to charge states of ions which when ionization without the supercharging reagent is performed, these charge states of ions are either, not present or is present in small quantities, such that fragmentation, and further analysis of these ions would not be possible.

Suitable supercharging reagents may include m-nitrobenzyl alcohol (m-NBA), sulfolane, dimethyl sulfoxide (DMSO), dimethylformamide (DMF), thiodiglycol, dimethylacetamide, dimethylsulfoxide, and N-methylpyrrolidone, glycerol and acetonitrile.

The supercharging reagent may be mixed with the eluent from the chromatography apparatus by any means. Methods of mixing the eluent and the supercharging reagent may include using a mixing tee or injecting the reagent into the eluent stream.

In some embodiments the mixing tee may be adapted to only allow the supercharging reagent to enter the eluent stream at selected times. This may be arranged to coincide with selected scans of the mass spectrometer. For example, the supercharging reagent may be arranged to only be allowed to enter the eluent stream so that the instrument may be ready to perform an ETD run at the time that part of the eluent stream reaches the instrument.

In one embodiment of the invention, the charge state of the glycopeptides ions to be used should be one charge higher than that capable of use for reactions without the presence of the supercharging reagent.

In one embodiment of the invention, the charge state of the glycopeptides ions to be used should be two charges higher than that capable of use for reactions without the presence of the supercharging reagent.

In one embodiment of the invention, the charge state of the glycopeptides ions to be used should be three or more charge higher than that capable of use for reactions without the presence of the supercharging reagent.

Although the description has been formed relating to ETD, the methods described may be equally applicable to Electron Capture Dissociation (ECD) and Proton Transfer Reactions (PTR) with only minor amendment.

In a further embodiment, covalent modification of primary amine groups in the gas phase by ion/ion reactions using N-hydroxysuccinimide (NHS) esters as the modifying reagents may be performed in accordance with the present invention. In this embodiment, the methods may be similar to those as described above for ETD, except the NHS ester, rather than the ETD reagent is input by Glow discharge.

In the case of PTR, a similar apparatus could be used, such that a PTR reagent (for example perfluoro-1,3,-diphenyl-cyclohexane (PDCH)) was ionised by glow discharge, rather than an ETD reagent. Other known methods of PTR may also be used, including PTR post ionisation in the ion source.

In one embodiment of the invention, the method of analysing the Glycopeptides and glycoproteins may comprise alternating between a first mode, where ETD is enabled on selected ion masses, a second mode, where substantially no fragmentation occurs and a third mode where all ions are subjected to ETD. This may give both precursor, and fragment ion information about all the ions present in the instrument at any time as well as the specific ion information relating to the 4+ ions.

The charge states suitable for use in accordance with the invention will vary dependent upon the analyte in question. In some embodiments the charge state may be 4+. In other embodiments the charge state may be 5+. In other embodiments the charge state may be 6+. In further embodiments the charge state may be 7+ or more.

In the case of time of flight instruments this may be consecutive pulses of the ToF pusher, or it may include multiple pulses of the T of pusher in a first mode to produce a mass spectrum then multiple pulses in a second mode to produce a second mass spectrum.

There are many methods of providing the mass analyser with ions produced by ETD, CID and (optionally) precursor ions either consecutively or simultaneously. These may be by having multiple parallel devices, by allowing some ions to bypass selected devices, by sending only some ions to reaction devices, or by varying conditions to allow fragmentation in only some cases.

In some embodiments the charge state is the highest possible where the peaks for parent ions (as shown in FIG. 3) are intense enough for analysis to be possible.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for the analysis of samples including one or more glycopeptides comprising:
    separating one or more glycopeptides using a chromatography system to produce a chromatographic eluent;
    adding a supercharging reagent to the chromatographic eluent between the chromatography system and a mass spectrometer;
    providing the chromatographic eluent with added supercharging reagent to the mass spectrometer;
    ionizing said chromatographic eluent with added supercharging reagent in an ion source of the mass spectrometer to produce glycopeptide ions;
    operating the mass spectrometer in at least a first mode, the first mode comprising:
        performing at least one ion ion reaction on at least some of the glycopeptide ions to produce fragment ions;
        mass analyzing the fragment ions to produce ion ion reaction mass spectral data;
        interpreting the ion ion reaction mass spectral data to provide structural information relating to the glycopeptides.

2. The method of claim 1 where the ion ion reaction is an Electron Transfer Dissociation reaction.

3. The method of claim 2 where Electron Transfer Dissociation is performed using an Electron Transfer Dissociation reagent selected from the group consisting of Fluoranthene, Azobenzene, 1,4-dicyanobenzene, 1,3-dicyanobenzene 1,4-nitrotoluene and nitrosobenzene.

4. The method of claim 1 where the ion ion reaction is an Electron Capture Dissociation reaction.

5. The method of claim 1 where the ion ion reaction is a Proton Transfer Reaction.

6. The method of claim 1 where the Supercharging reagent is selected from the group consisting of m-nitrobenzyl alcohol (m-NBA), sulfolane, dimethyl sulfoxide (DMSO), dimethylformamide (DMF), thiodiglycol, dimethylacetamide, dimethylsulfoxide, N-methylpyrrolidone, glycerol, and acetonitrile.

7. The method of claim 1 further comprising operating the mass spectrometer in at least a second mode, the second mode comprising:
    performing Collision induced dissociation on at least some of the glycopeptide ions to produce Collision induced dissociation fragment ions,
    mass analyzing the Collision induced dissociation fragment ions to produce Collision induced dissociation mass spectral data,
    interpreting the Collision induced dissociation mass spectral data to provide structural information relating to the glycopeptides.

8. The method of claim 7 further comprising operating the mass spectrometer in at least a third mode, the third mode comprising:
    performing substantially no fragmentation or reaction on at least some glycopeptide ions, mass analyzing the glycopeptide ions to produce precursor mass spectral data.

9. The method of claim 8 wherein the method comprises operating the mass spectrometer in the first, second, and third modes consecutively.

10. The method of claim 8 wherein the method comprises operating the mass spectrometer in both the first and second modes simultaneously and in the third mode consecutively.

11. The method of claim 7 wherein the method further comprises operating the mass spectrometer in both the first and second modes simultaneously.

12. The method of claim 7 wherein the method further comprises operating the mass spectrometer in the first and second modes consecutively.

13. The method of claim 1 wherein the step of adding a supercharging reagent to the chromatographic eluent between the chromatography system and the mass spectrometer is performed using a mixing tee.

* * * * *